United States Patent
Hennix et al.

(10) Patent No.: US 10,497,113 B2
(45) Date of Patent: Dec. 3, 2019

(54) TARGET-SPECIFIC DOSE AND SCATTER ESTIMATION IN CT IMAGES

(71) Applicants: Elekta AB (publ), Stockholm (SE); University Health Network, Toronto (CA)

(72) Inventors: Marcus Hennix, Huddinge (SE); Hakan Nordstrom, Sollentuna (SE); Markus Eriksson, Gustavsberg (SE); Jonas Adler, Solna (SE); David Jaffray, Etobicoke (CA); Gregory Bootsma, Toronto (CA); Frank Verhaegen, Riemst (BE); Bjorn Nutti, Solna (SE)

(73) Assignees: Elekta AB (publ), Stockholm (SE); University Health Network, Toronto (CA)

( * ) Notice: Subject to any disclaimer, the term of this patent is extended or adjusted under 35 U.S.C. 154(b) by 0 days.

(21) Appl. No.: 15/106,081

(22) PCT Filed: Dec. 18, 2014

(86) PCT No.: PCT/EP2014/078394
§ 371 (c)(1),
(2) Date: Jun. 17, 2016

(87) PCT Pub. No.: WO2015/091748
PCT Pub. Date: Jun. 25, 2015

(65) Prior Publication Data
US 2016/0314584 A1    Oct. 27, 2016

(30) Foreign Application Priority Data
Dec. 18, 2013   (GB) ................... 1322452.2

(51) Int. Cl.
*G06T 7/00*    (2017.01)
*A61B 6/03*    (2006.01)
(Continued)

(52) U.S. Cl.
CPC ............ *G06T 7/0012* (2013.01); *A61B 6/032* (2013.01); *A61B 6/5205* (2013.01);
(Continued)

(58) Field of Classification Search
CPC ..... A61B 6/032; A61B 6/5205; A61B 6/5282; G06T 5/00; G06T 5/002; G06T 5/50;
(Continued)

(56) References Cited

U.S. PATENT DOCUMENTS 6,256,367 B1   7/2001  Vartanian
6,618,466 B1*  9/2003  Ning .................. A61B 6/032
                                                378/62

(Continued)

OTHER PUBLICATIONS

Chan et al. "The validity of Monte Carlo simulation in studies of scattered radiation in diagnostic radiology." Physics in Medicine & Biology 28.2 (1983): 109. (Year: 1983).*

(Continued)

*Primary Examiner* — Katrina R Fujita
(74) *Attorney, Agent, or Firm* — Finnegan, Henderson, Farabow, Garrett & Dunner LLP (57) ABSTRACT

Embodiments disclose a method performed by at least one processor for processing a plurality of x-ray projection images of a subject, the method comprising a plurality of operations including reconstructing the projection images to yield a volume reconstruction; segmenting the reconstructed volume by assigning a material type to each voxel; estimating a first set of scatter images corresponding to a subset of the projection images by calculating probabilistic predictions of interactions of x-rays with the subject and applying (Continued)

a low pass spatial filter to the scatter images; estimating a second set of scatter images corresponding to projection images not included in the subset, based on the first set of scatter images; and subtracting, for each projection image, the corresponding scatter image to yield a corrected projection image. Applying the plurality of operations of the method in an iterative process on graphics-processor-quality computational hardware enables real-time scatter correction and reconstruction of CT volume images.

14 Claims, 4 Drawing Sheets (51) Int. Cl.
*A61B 6/00* (2006.01)
*G06T 5/50* (2006.01)
*G06T 5/00* (2006.01)
*G06T 11/00* (2006.01)
*G06K 9/52* (2006.01)
*G06K 9/62* (2006.01)
*G06T 7/20* (2017.01)
*G06T 7/10* (2017.01)

(52) U.S. Cl.
CPC .............. *A61B 6/5282* (2013.01); *G06K 9/52* (2013.01); *G06K 9/6215* (2013.01); *G06T 5/00* (2013.01); *G06T 5/002* (2013.01); *G06T 5/50* (2013.01); *G06T 7/10* (2017.01); *G06T 7/20* (2013.01); *G06T 11/003* (2013.01); *G06T 11/005* (2013.01); *G06T 11/008* (2013.01); *G06T 2207/10081* (2013.01); *G06T 2207/10116* (2013.01); *G06T 2207/20076* (2013.01); *G06T 2207/20112* (2013.01); *G06T 2207/20182* (2013.01); *G06T 2207/20224* (2013.01); *G06T 2207/30004* (2013.01)

(58) Field of Classification Search
CPC .......... G06T 7/0012; G06T 7/10; G06T 7/20; G06T 11/003; G06T 11/005; G06T 11/008; G06T 2207/10081; G06T 2207/10116; G06T 2207/20076; G06T 2207/20112; G06T 2207/20182; G06T 2207/20224; G06T 2207/3004; G06K 9/52; G06K 9/6215
See application file for complete search history.

(56) References Cited

U.S. PATENT DOCUMENTS

| 7,396,162 B1* | 7/2008 | Edic ..................... A61B 6/5282 378/207 |
| 7,729,473 B2 | 6/2010 | Jaffray et al. |
| 2003/0016851 A1* | 1/2003 | Kaufman ............... A61B 6/032 382/131 |
| 2005/0185753 A1* | 8/2005 | Du ....................... A61B 6/5282 378/7 |
| 2007/0086672 A1* | 4/2007 | Zeng ......................... G06T 5/20 382/261 |
| 2012/0288176 A1* | 11/2012 | Ye ......................... G06T 11/005 382/131 |

OTHER PUBLICATIONS

Schörner, Karsten. Development of methods for scatter artifact correction in industrial x-ray cone-beam computed tomography. Diss. Technische Universität München, 2012. (Year: 2012).*
Wiegert, Jens "Scattered radiation in cone-beam computed tomography: analysis, quantification and compensation." Publikations server der RWTH Aachen University (2007). (Year: 2007).*
International Search Report and Written Opinion in International Application PCT/EP2014/078394, dated Mar. 3, 2015.
Poludniowski et al., "An efficient Monte-Carlo-based algorithm for scatter correction in keV cone-beam CT." Phys. Med. Biol. 54:12 (Jun. 21, 2009), pp. 3847-3864.
Ning et al., "X-ray scatter correction algorithm for cone beam CT imaging," Med. Phys. 31:5 (May 1, 2004), pp. 1195-1202.
Colijn et al., "Accelerated Simulation of Cone Beam X-Ray Scatter Projections," IEEE Transactions on Medical Imaging 23:5, (May 1, 2004), pp. 584-590.
Ruhrnschopf et al., "A general framework and review of scatter correction methods in x-ray cone-beam computerized tomography. Part 1: Scatter compensation approaches," Med. Phys. 38:7 (Jun. 30, 2011), pp. 4296-4311.

* cited by examiner

Fig 10

TARGET-SPECIFIC DOSE AND SCATTER ESTIMATION IN CT IMAGES

CROSS-REFERENCE TO RELATED APPLICATION

This application is a national phase of International Application No. PCT/EP2014/078394, filed on Dec. 18, 2014, which claims priority to GB Application No. 1322452.2, filed on Dec. 18, 2013. The contents of the above-referenced applications are expressly incorporated herein by reference to their entireties.

FIELD OF THE INVENTION

The present invention relates to a method of estimating the effect of scatter in CT images, and to apparatus embodying that method. This can be used to prepare images in which the effect of that scatter is alleviated.

BACKGROUND ART

A CT reconstruction is a multi-dimensional image showing the internal structure of a patient or an object. It is prepared by taking numerous x-ray projections through the patient or object, which are then used in a computational process that calculates a structure that would have led to the collection of x-ray projections that was used.

Various forms of x-ray projection can be used. A single narrow beam (or "pencil beam") can be used which will measure the attenuation of the x-ray beam along it. This is then rotated around the patient or object so as the measure the attenuation along a series of directions. This allows the internal structure of a single "slice" to be determined, the slice being the plane in which the beam rotated. More commonly, a fan beam can be used, usually orienting the fan within the plane of the slice, which gives a one-dimensional projection offering more information than a single measurement. In both cases, the patient or object (or the x-ray apparatus) are indexed perpendicularly to the slice plane in order to capture an adjacent slice and thereby build up a three-dimensional image.

In another form of CT, known as "Cone-Beam CT" or CBCT, a cone of radiation is directed towards the patient or object and detected after attenuation by a two-dimensional flat-panel detector to yield a number of two-dimensional projection images. The radiation source and the detector are then rotated around the patient or object to give the necessary collection of images from multiple directions. These can then be used to reconstruct a three-dimensional volume image.

Regardless of the type of CT scanning, the mathematical algorithms used to create the images from the projections assume that the photons which arrive at a specific location in the projection image have been attenuated along a straight-line path from a point-like source of radiation. In practice, and especially for fan-beam and cone-beam CT, this is not the case due to scattering. When an x-ray photon interacts with matter, it can be attenuated (i.e. absorbed), or it can be scattered. In the latter case, the photon is re-emitted in a random direction, and therefore may be detected giving rise to an inaccurate measurement of the attenuation elsewhere in the projection image. Fortunately, x-ray scattering is a well-characterised phenomenon and is therefore relatively predictable given knowledge of the nature of the beam and the matter that it will be interacting with. A Monte-Carlo-type simulation can therefore be run, computing the outcome of a large number of random interactions between x-ray photons and the target to produce projection images of just the scattered radiation. These images can then be subtracted from the actual projection images captured by the apparatus, producing a set of clean (substantially scatter-free) projection images. These can be used to reconstruct a substantially scatter-free CT image.

U.S. Pat. No. 6,256,367 discloses such a scatter correction method for computed tomography images of general object geometries where the object geometry is not known a priori, by using the initial CT image (including scatter) as the basis for the Monte-Carlo simulation, which then yields an improved CT image with less scatter. That process can be iterated if necessary until the CT images being produced start to converge; U.S. Pat. No. 6,256,367 notes that convergence can be relatively swift.

SUMMARY OF THE INVENTION

Monte-Carlo simulations for removing scatter effects in CT images produce good results (especially in CBCT images) but take too long to produce. Ideally, for clinical use the cleaned image would be available within a minute or less. The sheer amount of computation needed in order to produce a Monte-Carlo result means that this is not possible with current computing technology, especially if multiple iterations are needed. Therefore we need a way of reducing the computational load that is involved, without having a noticeable effect on the quality of the simulation. The present invention suggests a way to reduce the computational burden which is able to bring the processing time down to an acceptable level.

Specifically, the invention is based on the appreciation that most of the contribution to a projection image from scatter effects lies in the low-frequency domain. In other words, the scatter image (i.e. the part of the image that is made up by scattered photons only) is generally a smoothly varying one without a great amount of fine detail. On the other hand, the random nature of a Monte-Carlo technique initially leads to a distribution that has strong high-frequency elements (visually, the distribution is "spiky") but which gradually smooths out as the computation proceeds, towards the correct profile. This realisation has two implications. First, we can interrupt the Monte-Carlo computation early and apply a low pass spatial filter to the predicted scatter image in order to remove the fine detail that is merely an artefact of the simulation process.

Thus, in this respect, the present invention provides a method of processing a plurality of x-ray projection images of a subject comprising the steps of preparing a volume image based on the plurality of projection images, using the volume image, estimating a plurality of scatter images corresponding to at least a subset of the projection images by calculating probabilistic predictions of interactions of x-rays with the subject, applying a low pass spatial filter to the scatter images, subtracting the filtered scatter images from each of the corresponding projection images to produce corrected projection images; and preparing a further CT volume image based on a set of projection images that includes the corrected projection images.

The second implication of the above-mentioned realisation is that the smoothly varying nature of the scatter image also applies between the projection images. Thus, whilst the scatter images corresponding to projection images captured from different directions do differ from each other, the variations in the scatter images as the direction changes are smooth variations rather than abrupt changes. This means that not all the scatter images need to be calculated from first principles. Instead, a limited set of scatter images can be calculated, and some or all of the remaining scatter images can be interpolated (or the like) from the directionally-adjacent scatter images.

The present invention therefore also provides, in a further aspect, a method of processing a plurality of x-ray projection images of a subject comprising the steps of preparing a CT volume image based on the plurality of projection images, using the volume image, estimating a first set of scatter images corresponding to a subset of the projection images by calculating probabilistic predictions of interactions of x-rays with the subject, estimating a second set of scatter images corresponding to the remaining projection images of the plurality, based on the first set of scatter images, subtracting the scatter images of the first and the second sets from each of the corresponding projection images to produce corrected projection images, and preparing a further CT volume image based on the corrected projection images.

Thus, the computational burden can be alleviated in two ways. First, the amount of computation needed to create an individual scatter image is reduced since the Monte-Carlo process can be stopped earlier than was otherwise the case, and the image then smoothed to create a usable scatter image. Second, the number of images that need to be computed is reduced since a proportion of the images can be inferred from the adjacent images. Together with state-of-the-art computational hardware such as modern graphics-processor units, this can yield a total processing time of less than one minute.

Of course, our preference is for both techniques to be employed. However, each technique offers a notable advantage over previously-known techniques and each can be used independently. In time, as the available computational power increases, it may be only be necessary to employ one or other of the techniques. However, where both techniques are used, the overall process becomes:
  i. reconstructing the projection images to yield a volume reconstruction
  ii. segmenting the volume by assigning a material type to each voxel
  iii. estimating a first set of scatter images corresponding to a subset of the projection images by calculating probabilistic predictions of interactions of x-rays with the subject, and applying a low pass spatial filter to the scatter images
  iv. estimating a second set of scatter images corresponding to the projection images not included in the subset, based on the first set of scatter images;
  v. for each projection image, subtracting the corresponding scatter image to yield a corrected projection image.

Ideally, steps (i) to (v) are iterated, with iterations subsequent to the first operating on the corrected projection images output from the previous iteration. After each iteration, the corrected projection images of that iteration can be compared with the corrected projection images of the previous iteration and, if the differences are below a threshold, the iteration is ceased.

A noise reduction algorithm can be applied to the projection images after step (iv), if felt necessary.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
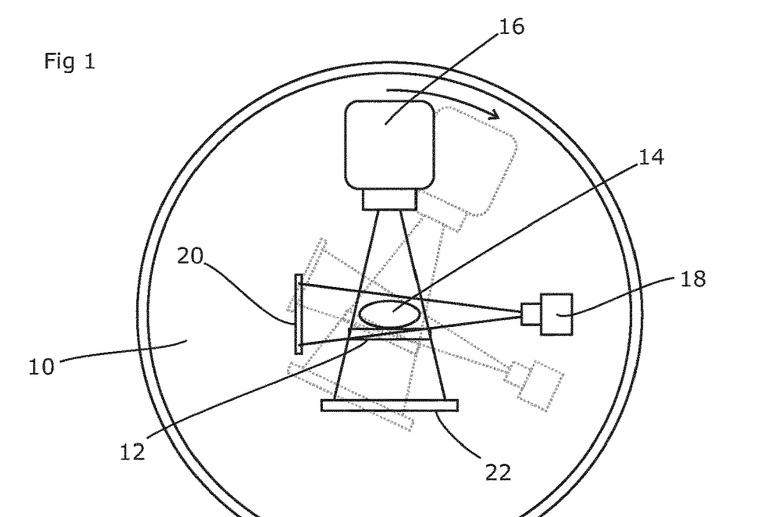
FIG. 1 shows a typical combined radiotherapy and CT scanning apparatus.

Referring to FIG. 1, a conventional radiotherapy apparatus is shown. This includes a vertically-arranged gantry 10 that is rotateable around a horizontal axis. A patient support 12 is placed just below that axis and carries a patient 14. The patient support 12 is typically adjustable in enough degrees of freedom to position the patient as required so that a target region of the patient is located correctly relative to the apparatus. A radiotherapy source 16 is mounted on the gantry 10 and emits a beam of therapeutic radiation towards the patient 14, typically of a photon energy of 1 MeV or above. Such radiation is harmful to tissue and, if properly directed, can have a therapeutic effect on lesions such as tumours within the patient. To maximise the effect of the radiation on the lesion and minimise its effect on the surrounding healthy tissue, the beam is collimated by collimators within the source 16, and the source itself is rotated by the gantry around the patient. The dose rate of the beam, its direction, and its collimation are all controlled during treatment according to a predetermined treatment plan in order to deliver a three-dimensional dose distribution to the patient.

To create the treatment plan, prior knowledge is needed of the internal structure of the patient, and to this end the apparatus also has a cone-beam CT scanning capability, This is provided by a diagnostic source 18 which is also mounted on the gantry 10 and directs a second beam towards the patient 14, of a significantly lower photon energy of 1-100 keV. This is detected after attenuation by the patient 14 by a flat-panel detector 20, mounted on the gantry 10 opposite the diagnostic source 18. Prior to treatment, the diagnostic source can be rotated around the patient in order to capture a series of two-dimensional projection images from a range of directions. These can then be reconstructed in a known manner by a suitably-programmed computing device in order to derive the internal structure that led to the projection images a so-called "computed tomography" or CT scan.

There may also be a second flat-panel detector 22 for the therapeutic beam, to provide some imaging capability and to act as a quality control check during treatment.

The above arrangement is usually known as a cone-beam CT scanner or CBCT scanner, as the beam used to obtain the projection images is a cone beam that projects a two-dimensional projection image on the detector 20. Other types of CT scanner use a fan beam that projects a one-dimensional image and a pencil beam that projects a single spot image; the present invention is equally applicable to these arrangements although the problem of scatter is more pronounced with CBCT. Equally, although the illustrated apparatus uses a linear-accelerator-based single radiation source, the invention is applicable to apparatus using other types of source, and to multiple-source devices such as our "Gammaknife" device employing multiple fixed sources as is (for example) described in U.S. Pat. No. 7,729,473.

Figure 2:
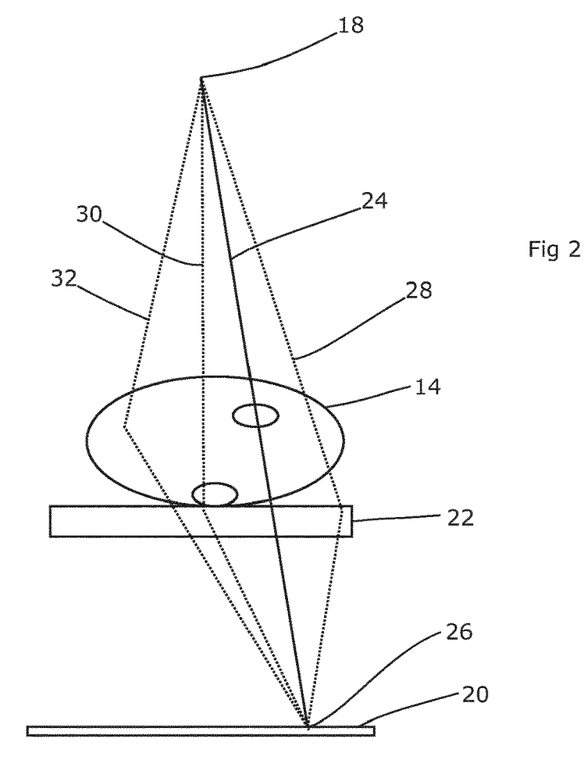
FIG. 2 illustrates scattering.
Figure 3:
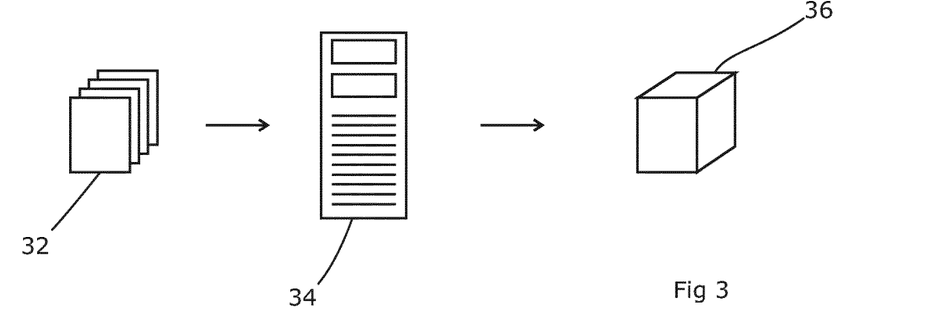
FIG. 3 illustrates existing methods of CT reconstruction.

Thus, the CT scan that is obtained can be used in the preparation of a treatment plan. A high-quality CT scan is therefore desirable in order to obtain a high-quality treatment plan. FIG. 2 illustrates one problem in doing so, that of scatter. The assumption that is made in reconstructing the CT volume image from the projection images is that the ray 24 is attenuated along a straight line from the source 18 to the point of impingement 26 on the flat panel detector 20, and likewise for all the other pixels in the detector 20. However, x-rays can be absorbed by matter that they interact with and then re-emitted as scattered radiation in a random direction. Thus, there may be other rays 28, 30, 32 which arrive at the same pixel 26 after having been scattered one or more times after interaction with the patient support or the patient. These will add to the beam intensity and affect the projection image. Thus, when the collection of projection images 32 (FIG. 3) are provided to the computational device 34 for reconstruction into a CT volume image 36, there will be artefacts in the volume image 36.

Figure 4:
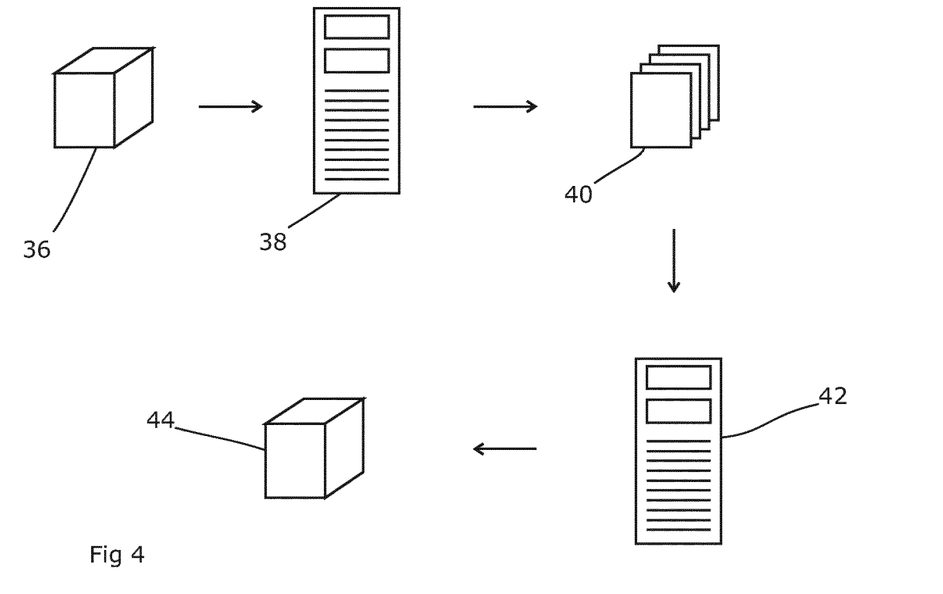
FIG. 4 illustrates existing methods of scatter estimation and correction.

This can be overcome computationally, by estimating the contribution to a projection image that is caused by scatter alone, as illustrated in FIG. 4. Starting from the volume image 36 (as suggested in U.S. Pat. No. 6,256,367) or from an a priori knowledge of the patient, patient support etc, or from a reasonable approximation to the patient and patient support (etc), a simulation can be run by a computational device 38 in which the path of a scattered photon is followed and its contribution to the projection image is recorded. This process is then repeated for a large number of photons, typically of the order of $10^9$ photons, after which a "scatter image" is produced, corresponding to the projection image taken in the same orientation that was used for the simulation, which shows only the part of the image produced by scatter effects. This scatter image can then be subtracted from the projection image in order to produce a corrected projection image that does not include scatter effects. The process can then be repeated to create a set of corrected projection images 40 which can be fed to a computational device 42 for reconstruction into a corrected CT volume image 44.

Where (as in U.S. Pat. No. 6,256,367) the first CT scan is used as the basis for the scatter estimation, it may be necessary to iterate the process using the corrected CT volume image as the basis for a second scatter estimation, to produce more accurate scatter images which can be subtracted from the original projection images to yield a basis for a further CT volume image.

Clearly, the volume of computation involved in this process is very large. However, when (as in FIG. 1) the process is conducted on a combined CT imaging and radiotherapy apparatus, it will be desirable to conduct the computation in real time so that after the projection images are captured, there is only a short delay of perhaps a minute or so before the results are available and the treatment can begin. It should be noted that preparation of the treatment plan is often a lengthy process, so the CT scan taken immediately prior to treatment will often be by way of a check that the patient is correctly positioned (and is the correct patient), and to detect any changes since the treatment plan was calculated that might require an adjustment of the treatment plan.

Figure 5:
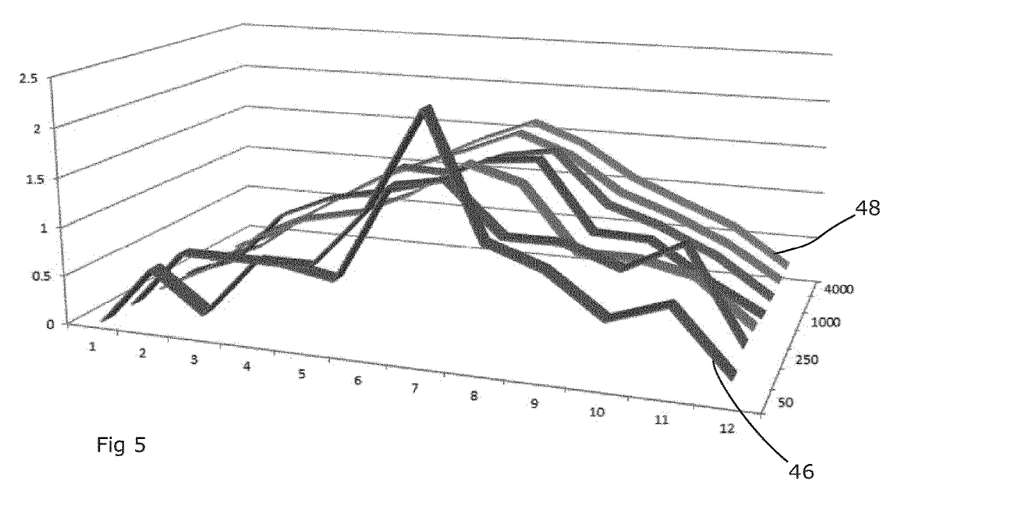
FIG. 5 is a simple example to show the development of Monte-Carlo simulations with further iteration.

FIG. 5 illustrates the principle behind one way of reducing the computational load. It shows the results of a simple example of a Monte-Carlo estimation, that of the prediction of the total of two standard six-sided dice. It is well known that the most likely result is 7 out of a maximum of 12, and therefore the profile to be expected is a peak at 7 dropping away either side towards the minimum value of 2 and the maximum of 12. FIG. 5 shows a series of profiles after simulating different numbers of throws of the dice. Thus, the frontmost profile 46 shows a result after 50 throws, behind which are the results at 100, 250, 500, 1000 and 2000 throws, ending at the rearmost profile 48 which is the result after 4000 simulated throws. It can be seen that the profile is initially quite irregular but eventually settles to a smooth profile after about 2000 throws. The earlier estimations all show a roughly correct profile, but have varying amounts of high-frequency noise within them.

Scatter is an analogous problem in that the result is a signal that is smoothly-varying. Therefore, we can take an earlier estimation, say at $10^6$ photons instead of $10^9$ photons, and apply a low-pass filter to remove the random irregularities that are an artefact of the Monte-Carlo process. Specifically, a low-pass filter in the frequency domain using a third-order 2D Butterworth filter defined as:

$$h(u, v) = \frac{1}{1 + \left(\left(\frac{2u}{u_{cut}}\right)^2 + \left(\frac{2v}{v_{cut}}\right)^2\right)^{N_B}}$$

can be used, where $u_{cut}$ and $v_{cut}$ are the cutoff frequencies, and $N_B$ is the order of the Butterworth filter. To determine the optimal filter cutoff values, a simple brute force optimization can be employed.

Figure 6:
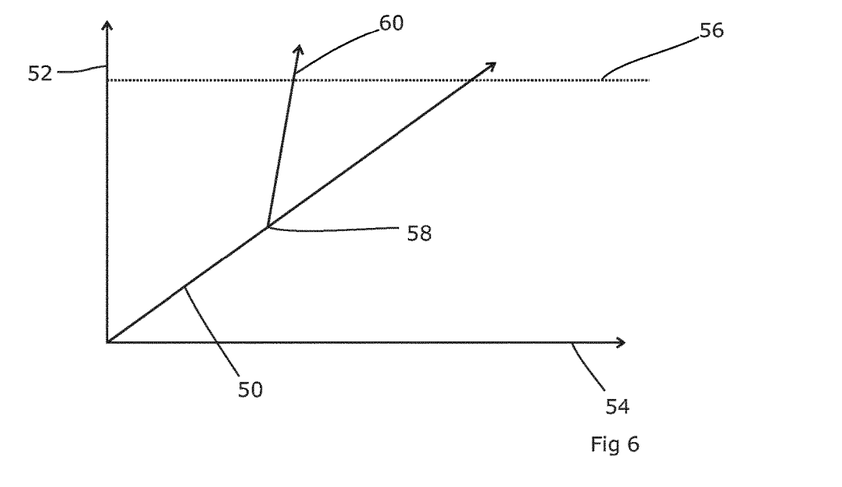
FIG. 6 illustrates the concept of the filtering technique of the present invention.

Thus, rather than waiting for the simulation to complete after running an ideal number of photon simulations, it can be interrupted early and brought to a useful quality level by applying the low-pass filter. FIG. 6 shows this very schematically; the progress of the simulation 50 is shown in terms of improving quality 52 as time 54 passes. Rather than wait for the simulation process alone to meet the necessary degree of accuracy 56, the simulation can be stopped early at 58 and the filter applied in order to produce a usable simulation at a much earlier stage 60.

Figures 7, 8, 9:
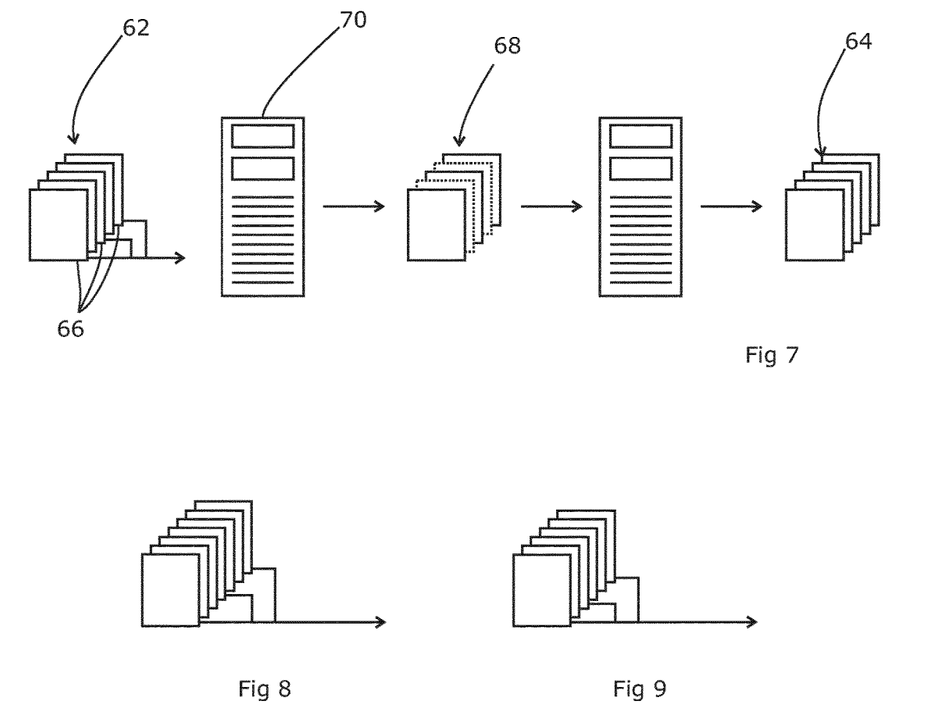
FIG. 7 illustrates the fitting technique of the present invention.
FIGS. 8 and 9 illustrate variations on the technique of FIG. 7.

In the same way that the scattering is smoothly-varying within one projection image, it is also smoothly-varying across projection images for similar reasons. Thus, as shown in FIG. 7, it is also possible to reduce the computational load by only computing a fraction of the necessary scatter images. A set of projection images 62 are fed into the computational process described above (FIGS. 3 and 4) for producing a set of scatter images 64. However, a scatter image is only prepared for every other projection image, in this case the first, third, fifth (etc) projection images 66 when the projection images are arranged in angular order. A deficient set 68 of scatter images is then produced by the computational process 70, containing scatter images corresponding to the first, third, fifth (etc) projection images. The intervening scatter images (i.e. corresponding to the second, fourth, sixth etc projection images) are then calculated by interpolation from the deficient set 68 to create a complete set 64. The data is interpolated using Fourier interpolation, a useful interpolation method for estimating a continuous signal from a set of discrete samples. Fourier interpolation can be computed efficiently by appropriately zero-padding the fast Fourier transform of a signal and then taking the inverse fast Fourier transform of the padded data. Importantly, the interpolation process is very much faster than the Monte-Carlo estimation process, even after shortening the Monte-Carlo process as described above.

FIG. 7 shows a scatter image being prepared for every other projection image, but this ratio is not necessarily essential. FIG. 8 shows a process based on estimating a scatter image for every third projection image, and FIG. 9 shows a process based on estimating scatter images for two out of every five projection images. Trial and error will determine what proportion and what pattern of scatter images needs to be calculated.

The overall process that can be followed is therefore as follows, letting the measured signal be q, the primary part p and the scatter s (thus q=p+s).

1. v1=R(q) where R( ) is the reconstruction operator giving an initial set of Hounsfield values for each voxel. These values will not be accurate as they do not allow for scatter
2. v1s=Seg(v1) Seg( ) is a function for segmenting the volume by assigning a material type to each voxel, to allow scatter prediction by the Monte Carlo simulation
3. s1=Sc(v1s) Monte Carlo determination of scatter contribution by the above techniques, run on a fast graphic processor unit
4. p1=q−s1 gives a first approximation to the primary contribution An optional step can be inserted at this point, of p1−>denoise(p1). As part of the signal has been subtracted from q, this means that the level of noise in p1 is likely to be higher than in q. Noise reduction algorithms may therefore assist in retaining the signal quality in $p_x$.

5. Go to 1, substituting p1 for q, to produce p2
6. Continue iterating, exiting when abs($p_n - p_{n-1}$)<ε

Figure 10:
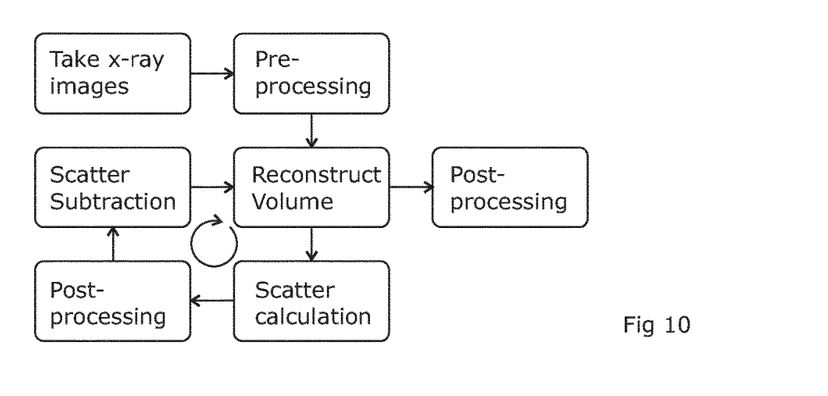
FIG. 10 summarises the processing process.

This is summarised on FIG. 10, starting from the top left. The initial x-ray images are acquired and are subjected to any necessary pre-processing to make them suitable for reconstruction. A volume is then reconstructed from those images, and is used as the basis for a scatter calculation as disclosed herein. The scatter images thus obtained are post-processed as necessary, for example to remove noise, and the scatter is subtracted from the x-ray images. A volume is then reconstructed from the corrected images, which will be a improved reconstruction as it is based on images that are less subject to scatter. This can therefore be used to create a better set of scatter images, and so the loop is completed once more. This can then continue until there is only a trivial (<ε) difference between the images for reconstruction produced by successive cycles, at which point it can be assumed that the process is complete. The volume image can then be subjected to any necessary post-processing.

It is thus important that all the steps are fast and that the convergence is fast. It is also notable that the process is self-contained, i.e. it does not require any added information from another image modality. By using the various methods for reducing the computation load, and performing both fast Monte Carlo calculations and quick reconstructions on a graphics processor unit, makes an "almost real time" iterated distribution correction for CBCT possible.

It will of course be understood that many variations may be made to the above-described embodiment without departing from the scope of the present invention.

The invention claimed is:

1. A method performed by at least one processor for processing a plurality of x-ray projection images of a subject, the method comprising a plurality of operations including:
   reconstructing the projection images to yield a volume reconstruction, wherein the plurality of projection images comprises at least a first subset of projection images and a second subset of projection images not included in the first subset;
   segmenting the reconstructed volume by assigning a material type to each voxel;
   estimating a first set of scatter images corresponding to the first subset of the projection images by:
      calculating probabilistic predictions of interactions of x-rays with the subject using a Monte Carlo process;
      determining a first threshold for completing the Monte Carlo process, wherein the first threshold represents a first number of photons for which to simulate scatter;
      determining a second threshold for completing the Monte Carlo process, wherein the second threshold represents a second number of photons for which to simulate scatter, the second number of photons being lower than the first number of photons;
      interrupting the Monte Carlo process when the process reaches the second threshold; and
      applying a low pass spatial filter to the estimated scatter images;
   estimating a second set of scatter images corresponding to the second subset of projection images, based on an interpolation from the first set of scatter images; and
   subtracting, for each projection image, the corresponding scatter image to yield a corrected projection image.

2. The method according to claim 1, further comprising:
   iterating the plurality of operations, wherein each iteration performs the plurality of operations on the corrected projection images output from a previous iteration.

3. The method according to claim 2, further comprising:
   comparing the corrected projection images of each iteration with the corrected projection images of the previous iteration;
   determining whether the differences between the compared images are below a third threshold; and
   stopping the iteration when the differences between the compared images are determined to be below the third threshold.

4. The method according to claim 1, further comprising:
   applying a noise reduction algorithm to the projection images after estimating the second set of scatter images.

5. The method according to claim 1, wherein the low pass spatial filter is a Butterworth filter.

6. The method according to claim 1, wherein the interpolation is a Fourier interpolation.

7. The method according to claim 6, wherein the low pass spatial filter is carried out in the Fourier domain.

8. A method performed by at least one processor for processing a plurality of x-ray projection images of a subject, the method comprising a plurality of operations including:
   generating a CT volume image based on the plurality of projection images, wherein the plurality of projection images comprises at least a first subset of projection images and a second subset of projection images, wherein the second subset of projection images are not included in the first subset;
   estimating, using the CT volume image, a first set of scatter images corresponding to at the first subset of the projection images by:
      calculating probabilistic predictions of interactions of x-rays with the subject using a Monte Carlo process;

determining a first threshold for completing the Monte Carlo process, wherein the first threshold represents a first number of photons for which to simulate scatter;

determining a second threshold for completing the Monte Carlo process, wherein the second threshold represents a second number of photons for which to simulate scatter, the second number of photons being lower than the first number of photons; and interrupting the Monte Carlo process when the process reaches the second threshold;

applying a low pass spatial filter to the first set of scatter images;

estimating a second set of scatter images corresponding to the second subset of projection images not included in the first subset, based on an interpolation from the first set of scatter images;

subtracting the filtered scatter images and the second set of scatter images from the corresponding projection images to produce corrected projection images; and generating an updated CT volume image based on a set of projection images that includes the corrected projection images.

9. A method performed by at least one processor for processing a plurality of x-ray projection images of a subject, the method comprising a plurality of operations including:

generating a CT volume image based on the plurality of projection images, wherein the plurality of projection images comprises at least a first subset of projection images and a second subset of projection images, wherein the second subset of projection images are not included in the first subset;

estimating, using the CT volume image, a first set of scatter images corresponding to the first subset of the projection images by:

calculating probabilistic predictions of interactions of x-rays with the subject using a Monte Carlo process;

determining a first threshold for completing the Monte Carlo process, wherein the first threshold represents a first number of photons for which to simulate scatter;

determining a second threshold for completing the Monte Carlo process, wherein the second threshold represents a second number of photons for which to simulate scatter, the second number of photons being lower than the first number of photons; and interrupting the Monte Carlo process when the process reaches the second threshold;

estimating a second set of scatter images corresponding to the second subset of the projection images, based on an interpolation of the first set of scatter images, wherein the second subset of projection images includes different projection images from the first subset of projection images;

subtracting the scatter images of the first set and the second set from the corresponding projection images to produce corrected projection images; and generating an updated CT volume image based on the corrected projection images.

10. The method according to claim 9, wherein estimating the first set of scatter images further includes applying a low pass spatial filter to the scatter images.

11. The method according to claim 10, wherein the low pass spatial filter is a Butterworth filter.

12. The method according to claim 9, wherein the second set of scatter images is estimated by interpolation from scatter images in the first set.

13. The method according to claim 9, wherein the projection images are two-dimensional.

14. The method according to claim 9, wherein the projection images are one-dimensional.

* * * * *